(12) United States Patent
Moran et al.

(10) Patent No.: US 8,439,942 B2
(45) Date of Patent: *May 14, 2013

(54) EMBOLIZATION DEVICE

(75) Inventors: Christopher J. Moran, Town & Country, MO (US); Thomas G. Kozma, Lafayette, IN (US); Umesh H. Patel, West Lafayette, IN (US); Mark W. Bleyer, West Lafayette, IN (US)

(73) Assignee: Cook Bioteck Incorporated, West Lafayette, IN (US)

( * ) Notice: Subject to any disclaimer, the term of this patent is extended or adjusted under 35 U.S.C. 154(b) by 72 days.

This patent is subject to a terminal disclaimer.

(21) Appl. No.: 12/959,799

(22) Filed: Dec. 3, 2010

(65) Prior Publication Data
US 2011/0077679 A1 Mar. 31, 2011

Related U.S. Application Data

(63) Continuation of application No. 10/718,155, filed on Nov. 20, 2003, now Pat. No. 7,857,825, which is a continuation of application No. 09/448,915, filed on Nov. 24, 1999, now abandoned.

(60) Provisional application No. 60/110,434, filed on Dec. 1, 1998.

(51) Int. Cl.
*A61M 29/00* (2006.01)
*A61F 2/06* (2006.01)

(52) U.S. Cl.
USPC ......... 606/200; 424/551; 424/600; 623/23.61

(58) Field of Classification Search ... 606/200; 424/551, 424/600; 623/1.11
See application file for complete search history.

(56) References Cited

U.S. PATENT DOCUMENTS

| | | |
|---|---|---|
| 2,127,903 A | 8/1938 | Bowen |
| 3,346,401 A | 10/1967 | Barat et al. |
| 3,562,820 A | 2/1971 | Braun |
| 3,649,163 A | 3/1972 | McCusker et al. |
| 4,292,972 A | 10/1981 | Pawelchak et al. |
| 4,347,234 A | 8/1982 | Wahlig et al. |
| 4,404,970 A | 9/1983 | Sawyer |
| 4,412,947 A | 11/1983 | Cioca |

(Continued)

FOREIGN PATENT DOCUMENTS

| | | |
|---|---|---|
| WO | WO 87/00062 | 1/1987 |
| WO | WO 94/03155 | 2/1994 |

(Continued)

OTHER PUBLICATIONS

American National Standard, ANSI/AAMI 10993-1:1994. "Biological Evaluation of Medical Devices—Part 1: Guidance on Selection of Tests." Association for the Advancement of Medical Instrumentation, pp. 9-17.

(Continued)

*Primary Examiner* — Vy Q Bui
(74) *Attorney, Agent, or Firm* — Woodard, Emhardt, Moriarty, McNett & Henry LLP

(57) ABSTRACT

A medical device (40) including a collagenous biomaterial (10) for causing embolus and treating an aneurysm. The collagenous biomaterial (10) includes a small intestine submucosa (12) that is configured into various components (16) for causing a vascular occlusion or a packing aneurysm lumen.

18 Claims, 6 Drawing Sheets

U.S. PATENT DOCUMENTS

| | | | |
|---|---|---|---|
| 4,512,342 A | 4/1985 | Zaneveld et al. |
| 4,606,337 A | 8/1986 | Zimmermann et al. |
| 4,681,588 A | 7/1987 | Ketharanathan |
| 4,705,517 A | 11/1987 | DiPisa, Jr. |
| 4,755,593 A | 7/1988 | Lauren |
| 4,795,741 A | 1/1989 | Leshchiner et al. |
| 4,798,611 A | 1/1989 | Freeman, Jr. |
| 4,801,299 A | 1/1989 | Brendel et al. |
| 4,813,958 A | 3/1989 | Dixon |
| 4,819,637 A | 4/1989 | Dormandy, Jr. et al. |
| 4,837,379 A | 6/1989 | Weinberg |
| 4,838,888 A | 6/1989 | Nashef |
| 4,866,132 A | 9/1989 | Obligin et al. |
| 4,885,005 A | 12/1989 | Nashef et al. |
| 4,891,359 A | 1/1990 | Saferstein et al. |
| 4,902,508 A | 2/1990 | Badylak et al. |
| 4,948,540 A | 8/1990 | Nigam |
| 4,950,483 A | 8/1990 | Ksander et al. |
| 4,956,178 A | 9/1990 | Badylak et al. |
| 4,969,912 A | 11/1990 | Kelman et al. |
| 4,970,298 A | 11/1990 | Silver et al. |
| 4,976,733 A | 12/1990 | Girardot |
| 4,994,069 A * | 2/1991 | Ritchart et al. ............... 606/191 |
| 4,994,084 A | 2/1991 | Brennan |
| 5,024,841 A | 6/1991 | Chu et al. |
| 5,028,695 A | 7/1991 | Eckmayer et al. |
| 5,094,661 A | 3/1992 | Levy et al. |
| 5,106,949 A | 4/1992 | Kemp |
| 5,141,747 A | 8/1992 | Scholz |
| 5,171,574 A | 12/1992 | Kuberasampath et al. |
| 5,206,023 A | 4/1993 | Hunziker |
| 5,206,028 A | 4/1993 | Li |
| 5,215,541 A | 6/1993 | Nashef et al. |
| 5,219,576 A | 6/1993 | Chu et al. |
| 5,222,970 A | 6/1993 | Reeves |
| 5,256,418 A | 10/1993 | Kemp et al. |
| 5,275,826 A * | 1/1994 | Badylak et al. ............... 424/551 |
| 5,279,612 A | 1/1994 | Eberhardt |
| 5,281,422 A | 1/1994 | Badylak et al. |
| 5,334,210 A | 8/1994 | Gianturco |
| 5,336,616 A | 8/1994 | Livesey et al. |
| 5,352,463 A | 10/1994 | Badylak et al. |
| 5,368,608 A | 11/1994 | Levy et al. |
| 5,372,821 A | 12/1994 | Badylak et al. |
| 5,374,515 A | 12/1994 | Parenteau et al. |
| 5,378,469 A | 1/1995 | Kemp et al. |
| 5,382,261 A | 1/1995 | Palmaz |
| 5,397,352 A | 3/1995 | Burres |
| 5,411,475 A | 5/1995 | Atala et al. |
| 5,411,887 A | 5/1995 | Sjolander |
| 5,413,791 A | 5/1995 | Rhee et al. |
| 5,443,478 A | 8/1995 | Purdy |
| 5,447,536 A | 9/1995 | Girardot et al. |
| 5,456,693 A | 10/1995 | Conston et al. |
| 5,460,962 A | 10/1995 | Kemp |
| 5,466,462 A | 11/1995 | Rosenthal et al. |
| 5,476,516 A | 12/1995 | Seifter et al. |
| 5,510,121 A | 4/1996 | Rhee et al. |
| 5,512,291 A | 4/1996 | Li |
| 5,514,181 A | 5/1996 | Light et al. |
| 5,516,395 A | 5/1996 | Anhauser et al. |
| 5,516,533 A | 5/1996 | Badylak et al. |
| 5,522,840 A | 6/1996 | Krajicek |
| 5,549,624 A | 8/1996 | Mirigian et al. |
| 5,554,389 A | 9/1996 | Badylak et al. |
| 5,565,210 A | 10/1996 | Rosenthal et al. |
| 5,571,181 A | 11/1996 | Li |
| 5,607,476 A | 3/1997 | Prewett et al. |
| 5,607,590 A | 3/1997 | Shimizu |
| 5,611,358 A | 3/1997 | Suval |
| 5,656,036 A | 8/1997 | Palmaz |
| 5,733,337 A | 3/1998 | Carr et al. |
| 5,830,879 A | 11/1998 | Isner |
| 5,925,062 A | 7/1999 | Purdy |
| 5,925,063 A | 7/1999 | Khosravi |
| 5,955,110 A | 9/1999 | Patel et al. |
| 6,096,052 A | 8/2000 | Callister et al. |
| 6,099,567 A | 8/2000 | Badylak et al. |
| 6,174,322 B1 | 1/2001 | Schneidt |
| 6,206,907 B1 | 3/2001 | Marino et al. |
| 6,206,931 B1 | 3/2001 | Cook et al. |
| 6,221,091 B1 | 4/2001 | Khosravi |
| 6,245,090 B1 | 6/2001 | Gilson et al. |
| 6,299,619 B1 | 10/2001 | Greene, Jr. et al. |
| 6,379,368 B1 | 4/2002 | Corcoran et al. |
| 6,432,116 B1 | 8/2002 | Callister et al. |
| 6,475,232 B1 | 11/2002 | Babbs et al. |
| 6,547,804 B2 | 4/2003 | Porter et al. |
| 6,589,256 B2 | 7/2003 | Forber |
| 6,592,566 B2 | 7/2003 | Kipke et al. |
| 6,645,167 B1 | 11/2003 | Whalen, II et al. |
| 6,746,426 B1 | 6/2004 | Flaherty et al. |
| 6,790,220 B2 | 9/2004 | Morris et al. |
| 2001/0041900 A1 | 11/2001 | Callister et al. |
| 2002/0010418 A1 | 1/2002 | Lary et al. |
| 2002/0058640 A1 | 5/2002 | Abrams et al. |
| 2002/0168265 A1 | 11/2002 | Stewart et al. |
| 2003/0051735 A1 | 3/2003 | Pavcnik et al. |
| 2003/0059372 A1 | 3/2003 | Whalen et al. |
| 2003/0082224 A1 | 5/2003 | Noujaim et al. |
| 2003/0120256 A1 | 6/2003 | Lary et al. |
| 2003/0153935 A1 | 8/2003 | Mialhe |
| 2003/0229366 A1 | 12/2003 | Reggie et al. |
| 2004/0044351 A1 | 3/2004 | Searle |
| 2004/0087930 A1 | 5/2004 | Whalen et al. |
| 2004/0087998 A1 | 5/2004 | Lee et al. |
| 2004/0093007 A1 | 5/2004 | Sussman et al. |
| 2004/0097901 A1 | 5/2004 | Whalen et al. |
| 2004/0143288 A1 | 7/2004 | Searle |
| 2004/0210249 A1 | 10/2004 | Fogarty |

FOREIGN PATENT DOCUMENTS

| | | |
|---|---|---|
| WO | WO 94/26175 | 11/1994 |
| WO | WO 95/22611 | 2/1995 |
| WO | WO 96/24661 | 8/1996 |
| WO | WO 96/25179 | 8/1996 |
| WO | WO 96/32146 | 10/1996 |
| WO | WO 97/19643 | 6/1997 |
| WO | WO 98/22158 | 5/1998 |
| WO | WO 98/25545 | 6/1998 |
| WO | WO 98/25636 | 6/1998 |
| WO | WO 98/25637 | 6/1998 |
| WO | WO 98/26291 | 6/1998 |
| WO | WO 99/44538 | 9/1999 |
| WO | WO 00/32112 | 6/2000 |
| WO | WO 00 32250 | 6/2000 |
| WO | WO 00/32253 | 6/2000 |

OTHER PUBLICATIONS

Baldry, M.G.C., et al., "Disinfection with Peroxygen", Industrial Biocides, 1988, pp. 91-116, K. Payne, editor, John Wiley & Sons, New York.

Block, S., "Peroxygen Compounds," Disinfection Sterilization and Preservation, 5th Ed. 2001, pp. 185-204. Lippincott Williams & Wilkins, Philadelphia, PA.

Denton, F.W., "Chlorhexidine," Disinfection, Sterilization and Preservation, 5th Ed. 2001, pp. 321-336. Lippincott Williams & Wilkins, Philadelphia, PA.

Horak, D., et al., "Hydrogels in Endovascular Embolization. III Radiopaque Spherical Particles, Their Preparation and Properties," Biomaterials, vol. 2, No. 8, pp. 142-145, Mar. 1, 1987. Elsevier Science.

* cited by examiner

EMBOLIZATION DEVICE

CROSS REFERENCE TO RELATED APPLICATIONS

This application is a continuation of application Ser. No. 10/718,155, filed Nov. 20, 2003, now U.S. Pat. No. 7,857,825 which is a continuation of application Ser. No. 09/448,915, filed Nov. 24, 1999, now abandoned which claims the benefit of U.S. Provisional Application No. 60/110,434, filed Dec. 1, 1998, each of which is hereby incorporated by reference.

TECHNICAL FIELD

The invention relates generally to a medical device and, in particular, to an embolization device.

BACKGROUND OF THE INVENTION

During the course of medical diagnosis, treatment, and the follow-up of various medical conditions, it is often necessary for the physician to block a certain blood vessel, deprive a certain area of life-sustaining blood, or fill a cavernous area in the blood vessel. For example, where a certain blood vessel is perforated, blood will flow out of the vessel into the local area causing a hemorrhage. For this condition, the physician will need to, inter alia, plug the perforation or occlude the vessel upstream of the perforation. In another example, where a tumor is located, one therapy for reducing the tumor or eliminating it completely is to occlude the vessel upstream of the tumor and deprive blood to the tumor. The tumor dies off. In both of these examples, a strategically placed thrombus or embolism completes the desired occlusion. However, the current state of technology requires man-made synthetic embolus, such as metal emboli, or other embolization-causing synthetic polymers. For example, polytetrafluoroethylene (PTFE) is a synthetic polymer often used in vascular graft prosthesis, but has been known to cause hyperplasia in the vessel. DACRON® material is another synthetic material often used in vivo vascular treatments, but like many synthetic materials, it can harbor microorganisms causing infection.

In the case of aneurysm treatment, an aneurysm is caused by a weakening of the vessel wall, which causes an invagination of the vessel wall. Blood flow is inhibited at the neck of the aneurysm due to turbulence caused by blood entering and exiting the lumen of the aneurysm. Current medical treatment of aneurysms include the use of metal coils, such as the FDA approved Gugliemi Detachable Coil, inserted into the lumen of the aneurysm. However, this platinum coil is relatively soft and does not provide a complete packing of the aneurysm lumen. It is not uncommon for the aneurysm to re-canalize, enlarge, and even rupture. Therefore, an aneurysm lumen filling device that packs the lumen sufficiently, is biocompatible, and promotes healing of the aneurysm would be well-received as reportedly approximately 28,000 patients suffer from intracranial aneurysms, of which 19,000 become severely disabled or die as a result of an aneurysm rupture. Furthermore, an embolization device that is soft enough to not puncture the vessel wall, yet strong enough to provide the necessary occlusion, are also desirable characteristics.

Tissue implants in a purified form and derived from collagen-based materials have been manufactured and disclosed in the literature. Cohesive films of high tensile strength have been manufactured using collagen molecules or collagen-based materials. Aldehydes, however, have been generally utilized to cross-link the collagen molecules to produce films having high tensile strengths. With these types of materials, the aldehydes can leech out of the film, e.g. upon hydrolysis. Because such residues are cytotoxic, the films are poor tissue implants.

Other techniques have been developed to produce collagen-based tissue implants while avoiding the problems associated with aldehyde cross-linked collagen molecules. One such technique is illustrated in U.S. Pat. No. 5,141,747 wherein the collagen molecules are cross-linked or coupled at their lysine epsilon amino groups followed by denaturing the coupled, and preferably modified, collagen molecules. The disclosed use of such collagen material is for tympanic membrane repair. While such membranes are disclosed to exhibit good physical properties and to be sterilized by subsequent processing, they are not capable of remodeling or generating cell growth or, in general, of promoting regrowth and healing of damaged or diseased tissue structures.

In general, researchers in the surgical arts have been working for many years to develop new techniques and materials for use as implants to replace or repair damaged or diseased tissue structures, for example, blood vessels, aneurysms, muscle, ligaments, tendons and the like. It is not uncommon today, for instance, for an orthopedic surgeon to harvest a patellar tendon of autogenous or allogenous origin for use as a replacement for a torn cruciate ligament. The surgical methods for such techniques are known. Further, it has been common for surgeons to use implantable prostheses formed from plastic, metal and/or ceramic material for reconstruction or replacement of physiological structures. Yet, despite their wide use, surgical implanted prostheses present many attendant risks to the patient.

Researchers have also been attempting to develop satisfactory polymer or plastic materials to serve as such functional tissue structures and/or other connective tissues, e.g., those involved in hernia and joint dislocation injuries. It has been discovered that it is difficult to provide a tough, durable plastic material which is suitable for long term connective tissue replacement. The tissues surrounding the plastic material can become infected and difficulties in treating such infections often lead to the failure of the implant or prostheses.

As mentioned above, various collagen-based materials have also been utilized for the above-mentioned tissue replacements; however, these materials either did not exhibit the requisite tensile strength or also had problems with infection and other immunogenic responses, encapsulation, or had other problems. In a related patent, U.S. Pat. No. 5,372,821, it is disclosed that a submucosa collagen matrix can be sterilized by conventional techniques, e.g., aldehyde tanning, propylene oxide, gamma radiation and peracetic acid. No specific processing steps are disclosed except that the submucosa layer is first delaminated from the surrounding tissue prior to sterilization treatment.

Some materials considered desirable are biological materials (biomaterials) from autogenous, allogenous, or xenogeneic (heteroplastic) sources. Biomaterials are desirable as they can be malleable and less likely to be rejected as foreign. One such biomaterial is collagen. Collagen is protein molecule that comes in many types. For example, collagen type I constitutes a significant amount of the collagen in the body. Type I is a heterotrimeric molecule, has a helical configuration, and is characterized by a Glycine-X-Y amino acid repeating sequence. Due to its abundance in the human body, collagen is being examined for its uses in medical treatment. One such treatment is for plugging vascular holes caused by the withdrawal of a catheter from the vessel. The collagen plug is inserted into the remaining hole as the hole begins to close up. In this manner the collagen plug remains in the hole with the adjacent tissue holding it in place.

SUMMARY OF THE INVENTION

The foregoing problems are solved and a technical advance is achieved in an illustrative embolization device advantageously utilizing a collagen based material. This collagen based material can be a biomaterial called Small Intestine Submucosa (SIS). SIS has been shown to be a remarkable biomaterial that promotes remodeling of the surrounding tissue, such as cellular invasion, host incorporation, and absorption of the SIS material into the local tissue. Furthermore, SIS has been shown to be acellular, strong, and exhibit a sidedness in that it has a differential porosity of its mucosal and serosal sides. SIS also does not trigger any negative immune system response as evidence suggests that it has no viral activity when checking for enveloped, non-enveloped, DNA, and RNA virus. Studies also show that SIS increases the Th-2 immune response by increasing the production of interleukin-10 over interferon-$\gamma$, which indicates that the immune response is more accommodation than rejection. Due to these and other properties, SIS makes for an excellent implantable biomaterial for use as an embolization or aneurysm treatment device. Furthermore, collagen is not currently being used as an embolization device or as an aneurysm lumen filling device, and in particular, SIS has not yet been used as such a device.

In accordance with the present invention, provided is a collagenous implantable biomaterial, that is further advantageous in that is promotes healing of the occluded area and healing of the aneurysm. Furthermore, as described herein, the collagenous biomaterial embolization device has been shown to obliterate aneurysms. Another ideal characteristic is that the device can cause new endothelial growth across the neck of the aneurysm, thus resulting in obliteration of the aneurysm.

In accordance with the present invention, provided is a collagenous embolization biomaterial in which the biomaterial has a biotropic agent comprising at least one of a proteoglycan, growth factor, glycoprotein, and glycosaminoglycan disposed thereon. Furthermore, this biomaterial may further comprise a biomaterial having pharmacologic agents or radiopaque agents disposed thereon. In accordance with the present invention, the biomaterial is preferably a collagenous biomaterial, such as pericardium, basement membrane, amniotic membrane, and more preferably a tissue mucosa, and even more preferably a tissue submucosa. In one embodiment of the invention, the biomaterial is small intestine submucosa.

DETAILED DESCRIPTION

Figure 1:
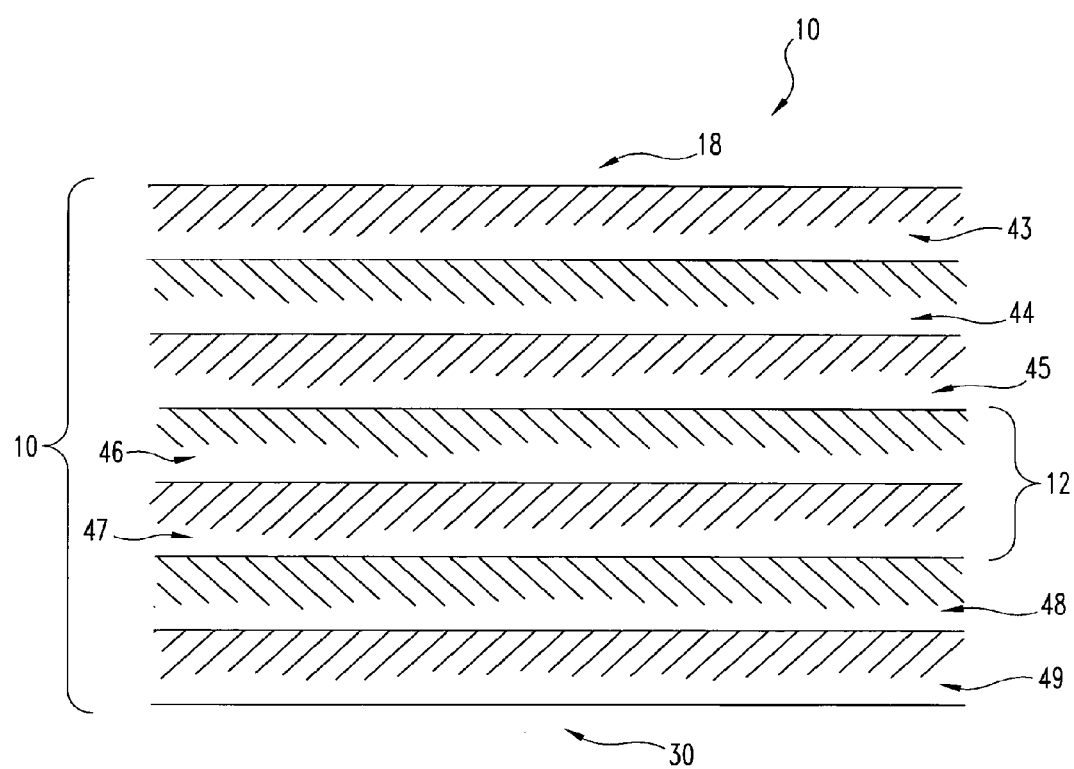
FIG. 1 represents a cross-sectional view of the layers of the small intestine.

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

In the discussions herein, a number of terms are used. In order to provide a clear and consistent understanding of the specification and claims, the following definitions are provided.

Bioburden—refers to the number of living microorganisms, reported in colony-forming units (CFU), found on and/or in a given amount of material. Illustrative microorganisms include bacteria, fungi and their spores.

Disinfection—refers to a reduction in the bioburden of a material.

Sterile—refers to a condition wherein a material has a bioburden such that the probability of having one living microorganism (CFU) on and/or in a given section of the material is one in one-million or less.

Pyrogen—refers to a substance which produces febrile response after introduction into a host.

Endotoxin—refers to a particular pyrogen which is part of the cell wall of gram-negative bacteria. Endotoxins are continually shed from the bacteria and contaminate materials.

Purification—refers to the treatment of a material to remove one or more contaminants which occur with the material, for instance contaminants with which the material occurs in nature, and/or microorganisms or components thereof occurring on the material. Illustratively, the contaminants can be those known to cause toxicity, infectivity, pyrogenicity, irritation potential, reactivity, hemolytic activity, carcinogenicity and/or immunogenicity.

Biocompatibility—refers to the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

Contaminant—refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

Tela submucosa—refers to a layer of collagen-containing connective tissue occurring under the mucosa in most parts of the alimentary, respiratory, urinary, integumentary, and genital tracts of animals.

The invention is generally directed to a medical device, comprising a biomaterial, for the endovascular treatment of aneurysms for example creating emboli in vessels, and, in particular, is further described in the non-limiting disclosure set forth below.

With reference to FIG. 1, the collagenous biomaterial 10 (also generally referred to as and including tissue mucosa, tissue submucosa, biomaterial, matrix, intestine) includes a plurality of histologically different cellular layers such as, for example, mesenteric layer 43, tunica serosa 44, tunica muscularis 45, tunica submucosa 46, lamina muscularis mucosa 47, stratum compactum 48, and lamina propria 49. Depending on which tissue system this collagenous biomaterial is harvested, this cellular layer structure can vary in the actual number of layers present. However, the collagenous biomaterial herein includes the Intestinal Collagen Layer described in U.S. Pat. No. 5,733,337 to Carr and in 17 Nature Biotechnology 1083 (November 1999). By way of example, collagenous biomaterial 10 is harvested from porcine small intestines. Of course the source of the collagenous biomaterial may be from any animal, such as of ovine, porcine, ovine or canine origin. Of particular interest is at least two of layers 46-48, known as tela submucosa 12, such as small intestine submucosa (SIS). This SIS structure is a multi-laminate structure, comprising at least two of the tunica submucosa 46, lamina muscularis mucosa 47, and the stratum compactum 48. The SIS 12 can be made using the techniques described generally in Cook et al., WIPO Publication WO 98/22158, dated 28 May 1998, which is the published application of PCT/US97/14855, the disclosure of which is set forth below. Other types of collagenous biomaterial or tissue also include the following, the disclosures of which are hereby expressly incorporated by reference: Gastric Submucosa as described in WO 98/26291 (PCT/US97/22729), claiming priority to U.S. Provisional application 60/032,686; Liver tissue as described in WO 98/25637 (PCT/US97/22727), claiming priority to 60/032,680; Stomach Submucosa as described in WO 98/25636 (PCT/US97/23010), claiming priority to 60/032,683; and Urinary Bladder Submucosa as described in U.S. Pat. No. 5,554,389.

Collagenous biomaterials 10 such as tela submucosa 12, as with many animal tissues, is generally aseptic in its natural state, provided the human or animal does not have an infection or disease. This is particularly the case since the tela submucosa 12 is an internal layer within the alimentary, integumentary, respiratory, urinary, and genital tracts of animals. Accordingly, it is generally not exposed to bacteria and other cellular debris such as the epithelium of the intestinal tract. One feature of the present invention is the discovery that by disinfecting the source tissue for the tela submucosa 12 prior to delamination, the aseptic state of the tela submucosa 12 layer can be preserved or substantially preserved, particularly if the delamination process occurs under sterile conditions.

In particular, it has been discovered that disinfecting the tela submucosa source, followed by removal of a purified matrix including the tela submucosa 12, e.g. by delaminating the tela submucosa 12 from the tunica muscularis 45 and the lamina propria 49 minimizes the exposure of the tela submucosa 12 to bacteria and other contaminants. In turn, this enables minimizing exposure of the isolated tela submucosa 12 to disinfectants or sterilants if desired, thus substantially preserving the inherent biochemistry of the tela submucosa 12 and many of the tela submucosa's beneficial effects.

A tela submucosa, implantable collagenous biomaterial 10 according to the present invention can, as indicated above, be obtained from the alimentary, respiratory, urinary, integumentary, or genital tracts of animals. Preferably, the tela submucosa tissues 12, which are collagen-based and thus predominantly collagen, are derived from the alimentary tract of mammals, such as cows, sheep, dogs, and most preferably from the intestinal tract of pigs. A preferred source of whole small intestine is harvested from mature adult pigs weighing greater than about 450 pounds. Intestines harvested from healthy, non-diseased animals will contain blood vessels and blood supply within the intestinal tract, as well as various microbes such as $E.\ coli$ contained within the lumen of the intestines. Therefore, disinfecting the whole intestine prior to delamination of the tela submucosa substantially removes these contaminants and provides a preferred implantable tela submucosa which is substantially free of blood and blood components as well as any other microbial organisms, pyrogens or other pathogens that can be present. In effect, this procedure is believed substantially preserve the inherent aseptic state of the tela submucosa, although it should be understood that it is not intended that the present invention be limited by any theory.

It is also desirable that the collagen matrix 10 according to the present invention be substantially free of any antiviral agents or any antimicrobial type agents which can affect the inherent biochemistry of the matrix 10 and its efficacy upon implantation. In the past, one method of treating such tissue material 10 is to rinse the delaminated tissue in saline and soak it in an antimicrobial agent, for example, as disclosed in U.S. Pat. No. 4,956,178. While such techniques can optionally be practiced with isolated submucosa 10 of the present invention, preferred processes according to present invention avoid the use of antimicrobial agents and the like which can not only affect the biochemistry of the collagen matrix 10 but also can be unnecessarily introduced into the tissues of the patient.

As discussed above, it has been discovered that a highly pure form of an implantable tela submucosa collagen matrix can be obtained by first disinfecting a tela submucosa 12 source prior to removing a purified collagen matrix including the tela submucosa layer, e.g. by delaminating the tela submucosa source. It has also been discovered that certain processing advantages as well as improved properties of the resultant tela submucosa layer are obtained by this process, including greater ease in removing attached tissues from the tela submucosa layer, and a characteristic, low contaminant profile.

Processes of the invention desirably involve first rinsing the tela submucosa source one or more times with a solvent, suitably water. The rinsing step is followed by treatment with a disinfecting agent. The disinfecting agent is desirably an oxidizing agent. Preferred disinfecting agents are peroxy compounds, preferably organic peroxy compounds, and more preferably peracids. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa matrices as described herein, preferably exhibiting a bioburden of essentially zero and/or essential freedom from pyrogens. In this regard, desirable processes of the invention involve immersing the tissue source (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

A preferred peroxy disinfecting agent is hydrogen peroxide. The concentration of hydrogen peroxide can range from about 0.05% to 30% by volume. More preferably the hydrogen peroxide concentration is from about 1% to 10% by volume and most preferably from about 2% to 5% by volume. The solution can or can not be buffered to a pH from about 5 to 9. More preferably the pH is from about 6 to 7.5. These concentrations can be diluted in water or in an aqueous solution of about 2% to about 30% by volume alcohol. Most preferably the alcohol is ethanol. The solution temperature can range from about 15 to 50° C. More preferably the solution temperature is from about 20 to 40° C. Most preferably, the solution temperature is from about 32 to 37° C. The exposure time can range from about 10 to 400 minutes. Preferably, the exposure time is from about 120 to 240 minutes. More preferably, the exposure time is from 180 to 210 minutes.

A preferred organic peroxide disinfecting agent is perpropionic acid. The concentration of perpropionic acid can range from about 0.1% to 10% by volume. More preferably the perpropionic acid concentration is from about 0.1% to 1.0% by volume and most preferably from about 0.2% to 0.5% by volume. These concentrations of perpropionic acid can be diluted in water or in an aqueous solution of about 2% to about 30% by volume alcohol. Most preferably the alcohol is ethanol. The tela submucosa tissue source can be exposed to the organic peroxide solution for periods from about 15 minutes to about 40 hours, and more typically in the range of about 0.5 hours to about 8 hours. Other peroxy disinfecting agents are suitable for use as described in "Peroxygen Compounds", S. Block, in *Disinfection, Sterilization and Preservation*, S. Block, Editor, 4th Edition, Philadelphia, Lea & Febiger, pp. 167-181, 1991; and "Disinfection with peroxygens", M. G. C. Baldry and J. A. L. Fraser, in *Industrial Biocides*, K. Payne, Editor, New York, John Wiley and Sons, pp. 91-116, 1988.

Another oxidizing disinfecting agent is chlorhexidine (1,6-di(4-chlorophenyldiguanido)hexane) in its digluconate form. The concentration of chlorhexidine digluconate can range from about 0.1% to 15% by weight. More preferably, the chlorhexidine digluconate concentration is from about 0.1% to 2% by weight and most preferably from about 0.2% to 5% by weight. The solution can or can not be buffered to a pH from about 5 to 8. More preferably the pH is from about 5.5 to 7. These concentrations can be diluted in water or in an aqueous solution of about 2% to about 20% by volume alcohol. Most preferably the alcohol is ethanol at a concentration of about 5% to 10%. The solution temperature can range from about 15 to 30° C. The exposure time can range from about 10 to 400 minutes. More preferably the exposure time is from about 30 to 60 minutes. Other chlorine agents are described in "Chlorhexidine", G. W. Denton, in *Disinfection, Sterilization and Preservation*, S. Block, Editor, 4th Edition, Philadelphia, Lea & Febiger, pp. 274-289, 1991.

In preferred preparative processes, a peracid or other disinfecting agent can be dissolved in a dilute aqueous alcohol solution, preferably wherein the alcohol has from 1 to about 6 carbon atoms, and wherein the alcohol can generally comprise from about 1% to about 30% by volume of the solution. More preferred alcohols for use in the invention are selected from the group consisting of ethanol, propanols and butanols. Ethanol is a most preferred alcohol for these purposes.

When a peracid is used in the disinfection, it is preferably selected from the group consisting of peracetic acid, perpropionic acid or perbenzoic acid. Peracetic acid is the most preferred disinfecting agent. The peracetic acid is preferably diluted into about a 2% to about 10% by volume alcohol solution. The concentration of the peracetic acid can range, for example, from about 0.05% by volume to about 1.0% by volume. Most preferably the concentration of the peracetic acid is from about 0.1% to about 0.3% by volume. Hydrogen peroxide can also be used as a disinfecting agent. Alternatively, or in addition, the tela submucosa tissue source, e.g. from small intestine, can be disinfected utilizing disinfecting agents such as glutaraldehyde, formalin and the like, which are also known for their ability to introduce substantial crosslinking into collagen matrices 10, in contrast to the action of other disinfecting agents such as peracids which can be used to disinfect without introducing such crosslinking. Additionally, the tela submucosa 12 source can be treated with radiation, e.g., gamma radiation, for purposes of disinfection.

Variations on the disinfection process can also include the following:
1. Intestine is treated with 0.2% peracetic acid, 5% ethanol solution at a ratio of 10:1 solution to intestine ratio by weight. Solution has a pH of 2.6. Solution and intestine are vigorously mixed for two hours.
2. Intestine is treated with 1% peracetic acid, 25% ethanol solution at a ration of 5:1 solution to intestine ratio by weight. Solution has a pH of 2. Solution and intestine are vigorously mixed for one hour.
3. Intestine is treated with 1% peracetic acid, 15% ethanol, and 10% hydrogen peroxide solution at a ratio of 5:1 solution to intestine ratio by weight. Solution and intestine are vigorously mixed for one hour.
4. Whole small intestine is rinsed four times with high purity water for 15 minutes. The intestine is then subjected to 1.5 MRAD Electron Beam radiation.
5. Whole small intestine is rinsed four times with high purity water for 15 minutes. Lengthwise along a conveyor belt, the intestine is subjected to high-intensity pulsed light which disinfects the intestine.

Following the treatment as described above, the tela submucosa layer is delaminated from its source, e.g., whole intestine, cow uterus and the like. It has been found that by following this post-disinfection-stripping procedure, it is easier to separate the tela submucosa layer from the attached tissues, e.g. at least from attached tunica muscularis tissue, as compared to stripping the tela submucosa layer prior to disinfection. Moreover it has been discovered that the resultant tela submucosa layer in its most preferred form exhibits superior histology, in that there is less attached tissue and debris on the surface compared to a tela submucosa layer obtained by first delaminating the tela submucosa layer from its source and then disinfecting the layer. Moreover, a more uniform tela submucosa tissue can be obtained from this process, and a tela submucosa having the same or similar physical and biochemical properties can be obtained more consistently from each separate processing run. Importantly, a highly purified, substantially sterile tela submucosa is obtained by this process.

The stripping of the tela submucosa source is preferably carried out by utilizing a disinfected or sterile casing machine, to produce a tela submucosa which is substantially sterile and which has been minimally processed. A suitable casing machine is the Model 3-U-400 Stridhs Universal Machine for Hog Casing, commercially available from the AB Stridhs Maskiner, Götoborg, Sweden. Therefore, the measured bioburden levels are minimal or substantially zero. Of course, other means for delaminating the tela submucosa source can be employed without departing from the present invention, including for example delaminating by hand.

It has also been discovered that more preferred processes according to the present invention, not only will eliminate or significantly reduce contaminants contained in the tela submucosa collagen matrix, but also will produce a tissue which exhibits no substantial degradation of physical and mechanical properties, e.g., differential porosity (i.e. wherein one side of the submucosa layer has greater porosity than the other side), and good strength, for example burst strength. Also, it has been discovered that more preferred processes do not affect the differential porosity of the tela submucosa collagen matrix which ultimately affects the level of efficacy of this tissue implant. For example, the tissue is not necessarily treated with a crosslinking agent or a material that disrupts the porosity or inherent, native structure of the collagen matrix. Moreover, when hydrogen peroxide is employed, the matrix as a whole has greater porosity as well as a higher oxygen content. This helps to ensure the absence of contaminants e.g., endotoxins, pyrogens and the like.

Preferred collagen-based matrices of the invention, preferably submucosa-containing matrices, are also characterized by the low contaminant levels set forth in Table 1 below, each contaminant level taken individually or in any combination with some or all of the other disclosed contaminant levels. The abbreviations in Table 1 are as follows: CFU/g=colony forming units per gram; PFU/g=plaque forming units per gram; µg/mg=micrograms per milligram; ppm/kg=parts per million per kilogram.

TABLE 1

| FEATURE | FIRST PREFERRED LEVEL | SECOND PREFERRED LEVEL | THIRD PREFERRED LEVEL |
|---|---|---|---|
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 µg/mg | <5 µg/mg | <2 µg/mg |
| VIRUS | <500 PFU/g | <50 PFU/g | <5 PFU/g |
| PROCESSING AGENT | <100,000 ppm/kg | <1,000 ppm/kg | <100 ppm/kg |

Even more preferred collagen-based matrices of the invention contain an endotoxin level of less than 1 EU/g, and most preferably less than 0.5 EU/g.

Purified collagen-based matrices according to the present invention can be processed in a number of ways, to provide collagenous matrices useful both in vitro and in vivo. For example, the submucosa can be configured to provide tissue grafts useful in vascular applications, e.g. as generally described in U.S. Pat. Nos. 2,127,903 and 4,902,508.

The tela submucosa 12 of the invention possesses mechanical properties highly desirable for tissue graft materials in vascular applications, including low porosity index, high compliance, and a high burst strength. One skilled in the art will appreciate that the preferred tissue graft material will be of low enough porosity to prevent intraoperative hemorrhage and yet of high enough porosity to allow extension of a newly-developed vasa vasorum through the graft material to nourish the neointimal and luminal surface.

Tela submucosa tissue of the present invention can also be processed to provide fluidized compositions, for instance using techniques as described in U.S. Pat. No. 5,275,826. In this regard, solutions or suspensions of the tela submucosa 12 can be prepared by comminuting and/or digesting the tela submucosa with a protease (e.g. trypsin or pepsin), for a period of time sufficient to solubilize the tissue and form substantially homogeneous solution. The submucosa starting material is desirably comminuted by tearing, cutting, grinding, shearing or the like. Grinding the submucosa 12 in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted tela submucosa 12 can be dried, for example freeze dried, to form a powder. Thereafter, if desired, the powder can be hydrated, that is, combined with water or buffered saline and optionally other pharmaceutically acceptable excipients, to form a fluid tissue graft composition, e.g. having a viscosity of about 2 to about 300,000 cps at 25EC. The higher viscosity graft compositions can have a gel or paste consistency.

Fluidized tela submucosa 12 of this invention finds use as an injectable heterograft for tissues, for example, bone or soft tissues, in need of repair or augmentation most typically to correct trauma or disease-induced tissue defects. The present fluidized submucosa 12 compositions are also used advantageously as a filler for implant constructs comprising, for example, one or more sheets of tela submucosa formed into sealed (sutured) pouches for use in cosmetic or trauma-treating surgical procedures.

In one illustrative preparation, tela submucosa 12 prepared as described herein is reduced to small pieces (e.g. by cutting) which are charged to a flat bottom stainless steel container. Liquid nitrogen is introduced into the container to freeze the specimens, which are then comminuted while in the frozen state to form a coarse tela submucosa 12 powder. Such processing can be carried out, for example, with a manual arbor press with a cylindrical brass ingot placed on top of the frozen specimens. The ingot serves as an interface between the specimens and the arbor of the press. Liquid nitrogen can be added periodically to the tela submucosa specimens to keep them frozen.

Other methods for comminuting tela submucosa specimens can be utilized to produce a tela submucosa powder usable in accordance with the present invention. For example, tela submucosa specimens can be freeze-dried and then ground using a manual arbor press or other grinding means. Alternatively, tela submucosa 12 can be processed in a high shear blender to produce, upon dewatering and drying, a tela submucosa powder.

Further grinding of the tela submucosa powder using a prechilled mortar and pestle can be used to produce consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

To prepare another preferred fluidized material, a tela submucosa powder can be sifted through a wire mesh, collected, and subjected to proteolytic digestion to form a substantially homogeneous solution. For example, the powder can be digested with 1 mg/ml of pepsin (Sigma Chemical Co., St. Louis Mo.) and 0.1 M acetic acid, adjusted to pH 2.5 with HCl, over a 48 hour period at room temperature. After this treatment, the reaction medium can be neutralized with sodium hydroxide to inactivate the peptic activity. The solubilized submucosa can then be concentrated by salt precipitation of the solution and separated for further purification and/or freeze drying to form a protease-solubilized intestinal submucosa in powder form.

Fluidized tela submucosa 12 compositions of this invention find wide application in tissue replacement, augmentation, and/or repair. The fluidized submucosal compositions can be used to induce regrowth of natural connective tissue or bone in an area of an existent defect. By injecting an effective amount of a fluidized submucosa composition into the locale of a tissue defect or a wound in need of healing, one can readily take advantage of the biotropic properties of the tela submucosa. Interestingly, fluidizing SIS 12 by comminution or enzymatic degradation does not result in any appreciable loss of biotropic activities, as shown in U.S. Pat. No. 5,275, 826 and does not appear to affect the biotropic agents 13, comprising at least one of a proteoglycan, glycoprotein, glycosaminoglycan, or growth factor.

It is also possible to shape large surface area constructs by combining two or more tela submucosa segments of the invention, for instance using techniques as described in U.S. Pat. No. 2,127,903 and/or International Publication No. WO 96/32146, dated 17 Oct. 1996, publishing International Application No. PCT/US96/04271, filed 5 Apr. 1996. Thus, a plurality of tela submucosa strips can be fused to one another, for example by compressing overlapping areas of the strips under dehydrating conditions, to shape an overall planar construct having a surface area greater than that of any one planar surface of the individual strips used to shape the construct. Shapes can be made by using sutures, staples, biocompatible adhesives such as collagen binding pastes, or dehydrating overlapping structures then heating the structure as described in U.S. Pat. No. 3,562,820.

The tela submucosa powder can be used alone, or in combination with one or more additional pharmacologic agents 14, such as physiologically compatible minerals, growth factors, antibiotics, chemotherapeutic agents, antigen, antibodies, genetic material, enzymes and hormones. Preferably, the powder-formed implant will be compressed into a predetermined, three-dimensional shape 16, which will be implanted into the bone region and will substantially retain its shape during replacement of the graft with endogenous tissues.

Tela submucosa 12 of the invention can also be used as a cell growth substrate, illustratively in sheet, paste or gel shape in combination with nutrients which support the growth of the subject cells, e.g. eukaryotic cells such as endothelial, fibroblastic, fetal skin, osteosarcoma, and adenocarcinoma cells (see, e.g. International Publication No. WO 96/24661 dated 15 Aug. 1996, publishing International Application No. PCT/US96/01842 filed 9 Feb. 1996. In preferred shapes, the tela submucosa substrate composition will support the proliferation and/or differentiation of mammalian cells, including human cells.

The inventive tela submucosa 12 can also serve as a collagenous matrix in compositions for producing transformed cells, (see, e.g., International Publication No. WO 96/25179 dated 22 Aug. 1996, publishing International Application No. PCT/US96/02136 filed 16 Feb. 1996; and International Publication No. WO 95/22611 dated 24 Aug. 1995, publishing International Application No. PCT/US95/02251 filed 21 Feb. 1995). Such compositions for cell transformation will generally include purified tela submucosa 12 of the present invention, for example in fluidized or paste shape as described in U.S. Pat. No. 5,275,826, in combination with a recombinant vector (e.g. a plasmid) containing a nucleic acid sequence with which in vitro or in vivo target cells are to be genetically transformed. The cells targeted for transformation can include, for example, bone progenitor cells.

In order to promote a further understanding of the present invention and its features and advantages, the following specific Examples are provided. It will be understood that these specific Examples are illustrative, and not limiting, of the present invention.

Example 1

Thirty feet of whole intestine from a mature adult hog is rinsed with water. This material is then treated in a 0.2% by volume peracetic acid in a 5% by volume aqueous ethanol solution for a period of two hours with agitation. The tela submucosa layer is then delaminated in a disinfected casing machine from the whole intestine. The delaminated tela submucosa 12 is rinsed four (4) times with sterile water and tested for impurities or contaminants such as endotoxins, microbial organisms, and pyrogens. The resultant tissue was found to have essentially zero bioburden level. The tela submucosa layer separated easily and consistently from the whole intestine 10 and was found to have minimal tissue debris on its surface.

Example 2

A ten foot section of porcine whole intestine is washed with water. After rinsing, this section of tela submucosa intestinal collagen source material is treated for about two and a half hours in 0.2% peracetic acid by volume in a 5% by volume aqueous ethanol solution with agitation. Following the treatment with peracetic acid, the tela submucosa layer is delaminated from the whole intestine. The resultant tela submucosa 12 is then rinsed four (4) times with sterile water. The bioburden was found to be essentially zero.

Example 3

A small section of the tela submucosa intestinal collagen material was subcutaneously implanted in a rat. Within 72 hours, significant angiogenesis was observed.

Example 4

Two sections of small intestine are processed by differing methods. The first section is rinsed in tap water, disinfected for 2 hours in a 5% by volume aqueous ethanol solution comprising 0.2% by volume peracetic acid, pH approximately 2.6, delaminated to the tela submucosa 12, rinsed in purified water, divided into two samples and rapidly frozen. The second section is rinsed in tap water, delaminated to the tela submucosa, rinsed in purified water, placed in a 10% neomycin sulfate solution for 20 minutes (as described in U.S. Pat. No. 4,902,508), rinsed in purified water, divided into two samples and rapidly frozen. The four above-prepared samples are tested for bioburden and endotoxin levels. The first two samples each have bioburdens of less than 0.1 CFU/g and endotoxin levels of less than 0.1 EU/g. The second two samples have respective bioburdens of 1.7 CFU/g and 2.7 CFU/g and respective endotoxin levels of 23.9 EU/g and 15.7 EU/g.

Example 5

Three sections of small intestine are processed by differing methods. The first is rinsed in tap water, disinfected for 2 hours in a 5% by volume aqueous ethanol solution comprising 0.2% by volume peracetic acid, pH about 2.6, delaminated to the tela submucosa, rinsed in purified water, and rapidly frozen. The second is rinsed in tap water, delaminated to the tela submucosa, rinsed in purified water, disinfected according to the methods of Example 1 in U.S. Pat. No. 5,460,962 (treatment for 40 hours in a 0.1% by volume aqueous solution of peracetic acid, buffered to pH 7.2), and rapidly frozen. The third is rinsed in tap water, delaminated to the tela submucosa, rinsed in purified water, disinfected according to the methods of Example 2 in U.S. Pat. No. 5,460,962 (treatment in 0.1% by volume peracetic acid in high salt solution, buffered to pH 7.2), and rapidly frozen. All three samples were tested for endotoxins. The endotoxin levels were <0.14 EU/g for the first sample, >24 EU/g for the second sample, and >28 EU/g for the third sample.

Example 6

Two sections of porcine small intestine were infected with 7×10$^6$ plaque forming units (PFU) of virus. Both were exposed to a 0.18% peracetic acid, 4.8% aqueous ethanol solution at a nine-to-one weight ratio of solution to material. A first sample was immersed in this solution for 5 minutes; the second was immersed for 2 hours. The material processed for 5 minutes exhibited 400 PFU per gram of material. The material processed for 2 hours exhibited zero PFU per gram of material.

Example 7

Purified tela submucosa 12, prepared as described herein, was tested to determine its nucleic acid content. Four samples of material weighing 5 mg each were subjected to DNA/RNA extraction as detailed in the DNA/RNA Isolation Kit by Amersham Lifescience Inc., Arlington Heights, Ill. Nucleic acid quantitation was performed by spectrophotometric determination of solution optical densities at 260 nm and 280 nm. The average nucleic acid content was 1.9±0.2 mg per milligram of material.

Small intestinal submucosa, prepared as described by U.S. Pat. No. 4,902,508, was tested to determine its nucleic acid content. Four samples of material weighing 5 mg each were subjected to DNA/RNA extraction as detailed in the DNA/RNA Isolation Kit by Amersham. Nucleic acid quantitation was performed by spectrophotometric determination of solution optical densities at 260 nm and 280 nm. The average nucleic acid content was 2.4±0.2 mg per milligram of material.

Example 8

Sections of tela submucosa 12 prepared according to the methods described herein were sent to an independent testing laboratory (NamSA, Inc., Northwood, Ohio) for biocompatibility testing as described in the standard ISO 10993. The samples were tested for USP Acute Systemic Toxicity, USP Intracutaneous Toxicity, Cytotoxicity, LAL Endotoxin, material-mediated Pyrogenicity, Direct Contact Hemolysis, and Primary Skin Irritation. The samples passed all tests, indicating that the material is biocompatible.

Example 9

One of its intended use is for human embolization and aneurysm treatment and as such must conform with FDA standards for safety and efficacy, of which the endotoxin level must comply with certain specifications. Using the procedure set forth in U.S. Pat. No. 5,460,962, two samples were analyzed. The first Kemp sample indicated an endotoxin level greater than 24 endotoxins units per gram and the second Kemp sample indicated an endotoxin level greater than 28 endotoxin units per gram. Thus, when using the procedure set forth in Kemp '962, the endotoxin levels fall outside the biocompatibility levels.

Example 10

Using the procedures set forth in U.S. Pat. Nos. 4,902,508 and 5,372,821 issued to Badylak, the endotoxin level shown ranges as high as 23.9 endotoxin units per gram per sample. This falls outside the permissible range and thus does not the meet the criteria of biocompatibility. The invention, prepared in the above prescribed manner of disinfection first then delamination, was observed to have an endotoxin level of less than 12 endotoxin units per gram, and more particularly, reported an endotoxin level of less than 5 endotoxin units per gram. Thus, the material of the present invention is biocompatible as defined above.

Example 11

Using a dog aneurysm model that has been used for over 40 years, two aneurysms were created in four dogs using segments of the external jugular vein attached in an end to side fashion on the common carotid artery. One aneurysm served as the control whilst the other served as the collagenous biomaterial treated aneurysm. In the collagenous biomaterial treated aneurysm, coils of radiopaque tela submucosa were inserted into the lumen of the aneurysm. The animals were sacrificed at day 29, 42, 62, and 78 and the aneurysms were excised for pathologic analysis. The control aneurysms were all patent and did not contain any thrombus. The treated aneurysms were partially filled with SIS and about the SIS was fibrotic tissue, granulation tissue, and rare foreign body giant cells. However, more importantly the neck of the lumen was covered with an endothelial lining of organized fibrous tissue and this surface was free of thrombus. Furthermore, analysis indicated that the lumen of the aneurysm was nearly filled. Thus, aneurysm obliteration occurred.

Figure 2:
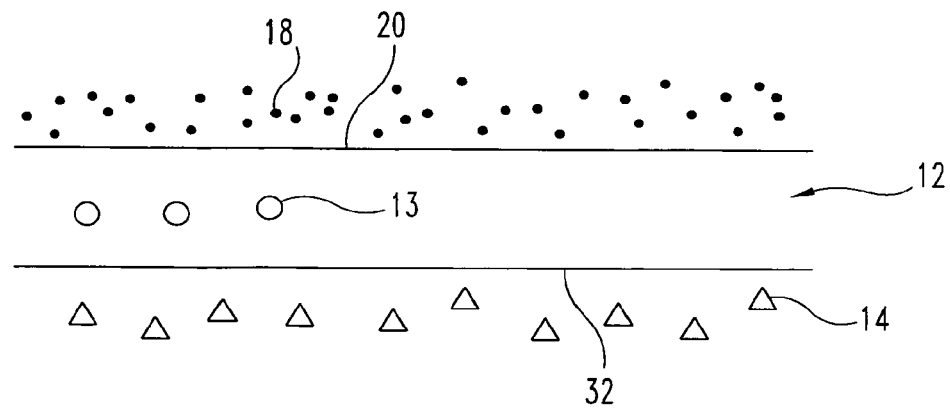
FIG. 2 represents the disposition of the pharmacologic agents on the invention.
Figure 3:
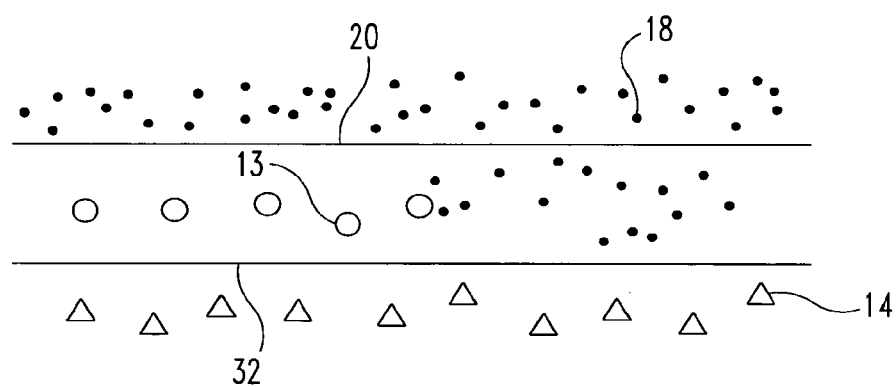
FIG. 3 represents the disposition of the radiopaque marker on the biomaterial.

With reference to FIGS. 2 and 3, a collagenous biomaterial, such as tela submucosa 12 can be made radiopaque by a variety of conventional procedures. In one embodiment of the invention, the collagen material is made into sheets 16, either in lyophilized or non-lyophilized form. Any radiopaque substance 18, including but not limited to, tantalum such as tantalum powder, can be spread along the surface of the tela submucosa 12. Other radiopaque materials 18 comprise bismuth, iodine, and barium, as well as other conventional markers. As used herein, the term "disposed" on shall be construed to include disposed on, disposed throughout, disposed in, disposed with, disposed along with, applied on, applied with, applied through, applied in, applied in conjunction with, and the like. With particular reference to tela submucosa 12, the differential porosity of the material can enable more radiopaque material 18 to be disposed on the tela submucosa 12. In one particular embodiment, tantalum powder 18 was disposed on a sheet 16 of tela submucosa 12 by rubbing it onto the serosal side 20 of the tela submucosa 12. To create a thrombogenic component, the tela submucosa 12 was then made into various components, such as, but not limited to, having a brush-like, braided, branched, helical, spherical, cubic, cylindrical, tubular, injectable, randomized, layered, and sheet-like component. For example, an injectable form of the invention can be readily made by comminuting the invention into small fibrils, fragments, or the like, then suspending them in solution, such as, but not limited to, a biocompatible gelatin suspension. Due to the viscosity of the gelatin suspension, the invention, when injected into the lumen of an aneurysm, will stay in the lumen and provide the therapeutic benefit to the aneurysm. The thrombogenic component is so made to either partially or fully cause occlusion of the vessel, to cause emboli formation, or to pack (or fill) an aneurysm lumen.

Figure 4:
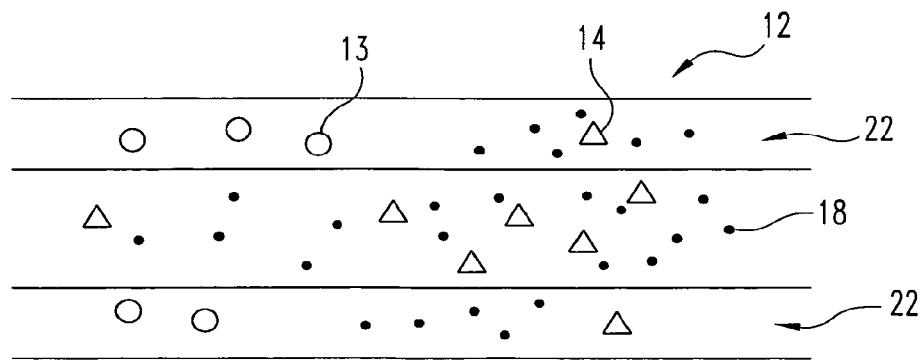
FIG. 4 represents another embodiment featuring a multi-laminate form of the invention.

With reference to FIG. 4, the invention can be made in layers 22. In this manner, the collagenous material including tela submucosa 12 can increase its structural integrity, strength, and applicability. In one embodiment of the invention, a dual layer of collagenous biomaterial can be used in sheets and disposed in between is the either the radiomarker 18 or pharmacologic agent 14, or both.

Figure 5:
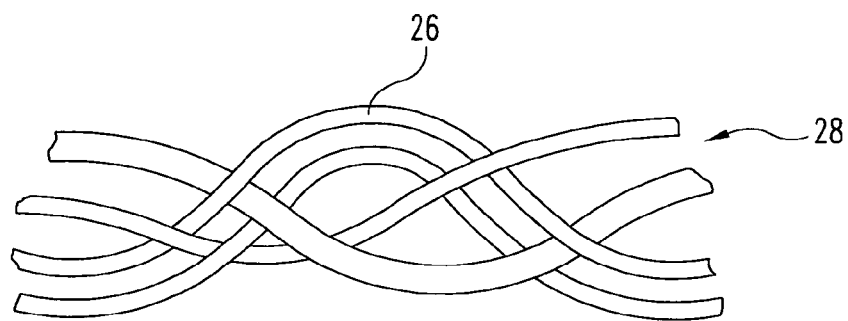
FIG. 5 represents the braid configuration of one embodiment of the invention.
Figure 6:
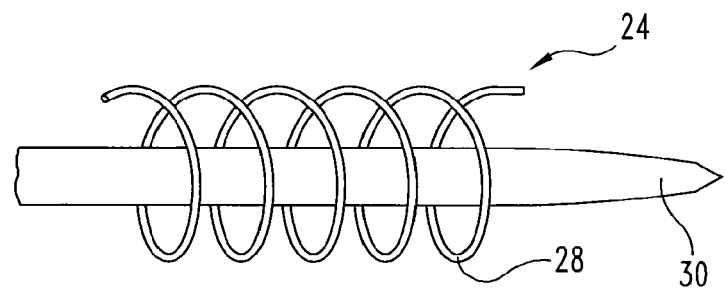
FIG. 6 represents the coiled configuration of one embodiment of the invention.

The collagenous biomaterial 10 of the present invention can be in lyophilized or non-lyophilized form. Where the biomaterial 10 is lyophilized, the biomaterial 10 has shape memory in that upon rehydration of anhydrous material, the material will reform into its freeze-dried shape. For example, one embodiment of the present invention includes the coil component 24. Strips 26 of the biomaterial can be shaped into a braid 28, as seen in the exemplary FIG. 5, to increase its strength or size. The coil component 24, though, is not limited to multiple strip 26 braids 28, as coils 24 can be shaped with one strip 26. The braided material 28 can then be wound around a mandrel 30, as seen in the exemplary FIG. 6, to shape a coil 24. The coil component 24 is then lyophilized by freeze-drying the coil 24 and dehydrating the coil 24 under vacuum pressure. The coil 24 then retains shape memory. The coil 24 then can be re-hydrated in a solution to become malleable again and will retain its shape memory. For example, after the coils 24 are made and dehydrated, the anhydrous coil 24 can then be unwound or crumpled up to facilitate delivery to the situs via a delivery catheter. When the coil 24 comes in contact with the body fluids, it will re-hydrate and reshape into a coil 24. In this manner, delivery of coils 24 to an aneurysm lumen is greatly facilitated. Furthermore, when used as an embolization device, the device can be readily inserted proximal to the targeted occlusion area and will reshape into the desired shape at the desired occlusion situs.

In similar fashion, the pharmacologic agent 14 can be disposed on the collagenous material. As used herein, the pharmacologic agent 14 includes, but is not limited to, growth factors, proteins, glycoproteins; proteoglycans, glycosaminoglycans, physiological compatible minerals, antibiotics, chemotherapeutic agents, enzymes, drugs, genetic material, and hormones. The agent 14 can be disposed on the serosal 20 or mucosal 32 sides of the submucosa 12, or can be disposed on the same or opposite sides of the collagenous material. Consideration of placement can be important depending on the desired shape 16 of the final device. For example, where the shape 16 is tubular, it can be desirable to place the pharmacologic agent 14 on the abluminal surface since that surface will be in contact with the surrounding tissue. On the other hand, if systemic release of the agent 14 is contemplated, then the agent can be placed on the lumenal side to permit the blood to contact the agent 14 and carry it away. Utilizing the braid shape 28, each individual strip 26 can be treated with different agents.

In one particular embodiment of the invention, a urinary bladder collagenous material was prepared by removing the abluminal layer and at least the tunica mucosal layer of the bladder. The delaminated collagenous material 10 was then treated with a pharmacologic agent 14 and a radiopaque marker 18, such as tantalum.

Figure 7:
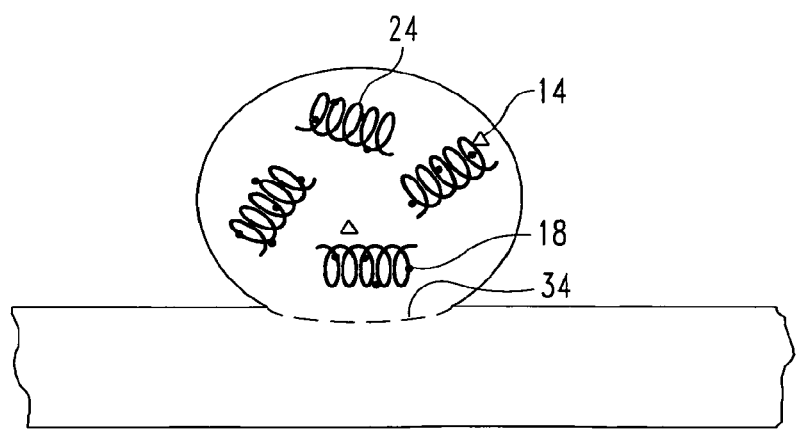
FIG. 7 illustrates the coiled configuration in the lumen of an aneurysm.

With reference to FIG. 7 and to EXAMPLE 11, shown is one embodiment of the invention. Shown is collagenous biomaterial with radiopaque material 18 disposed thereon and configured into coil component 24 that is positional in the lumen of an aneurysm. Also shown are the healing properties of the biomaterial in which a new thin endothelial lining 34 is created. Preferably, components that fill the lumen of the aneurysm are desirable. Furthermore, the biomaterial can be treated with pharmacologic agents 14 described herein to treat the aneurysm in general, and any other problems in particular.

Figure 8:
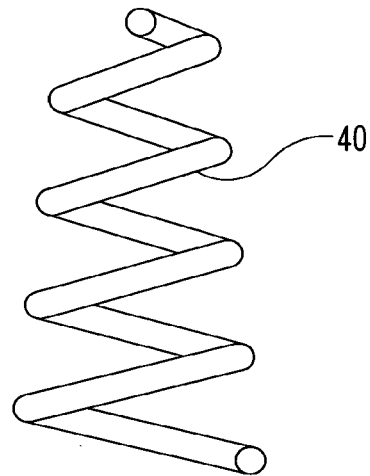
FIG. 8 depicts an illustrative embolization device of the present invention.
Figure 9:
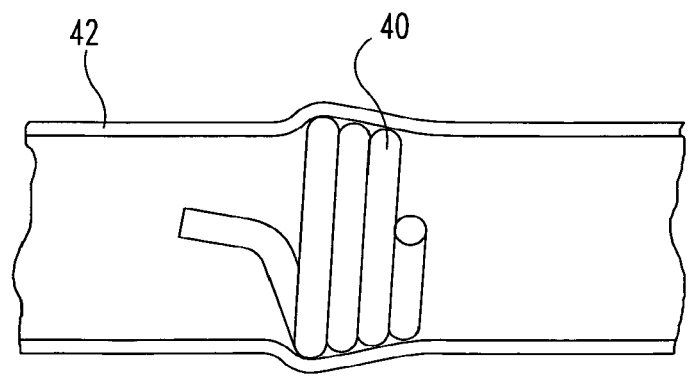
FIG. 9 depicts the embolization device of FIG. 8 disposed and collapsed in a blood vessel.

FIG. 8 depicts an illustrative embodiment of embolization device 40 of the present invention in the configuration of a frustoconical helical coil of which the turns overlap each other. Although depicted in a relaxed and expanded form, the turns of device collapse upon themselves to occlude a blood vessel 42 as depicted in FIG. 9.

In yet another embodiment of the present invention, the invention may comprise a tapered embolization coil. Often times it is necessary to occlude a blood vessel that progressively narrows. The embolization device may be configured to include central backbone with tapering spirals. For example, spirals at a proximal end will have a larger diameter than spirals occurring at the distal end. This embodiment is different than the other embodiments described herein has this embodiment comprises a central backbone with spirals versus a single, continuous wire. The spirals or the central backbone may also have fibrils on it to increase thrombogenicity.

Figure 10:
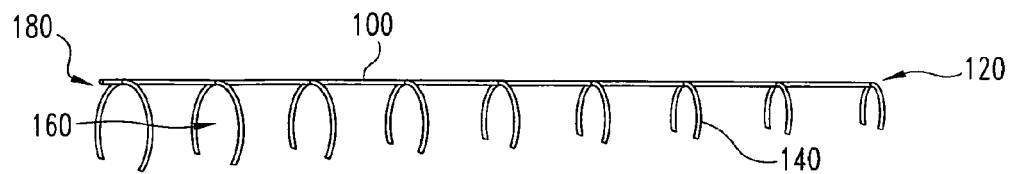
FIGS. 10-16 depict yet another embodiment of the invention.
Figure 13:
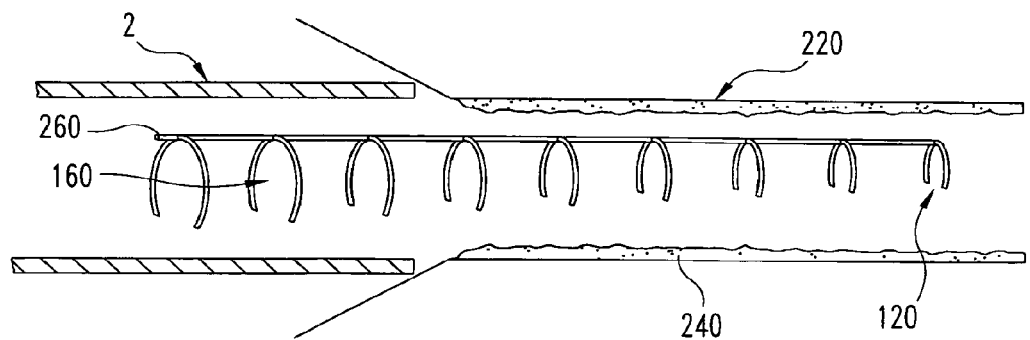

With reference to FIGS. 10 and 13, tapered device has a central backbone 100. The backbone 100 runs longitudinal and can terminate at one end, such as at the distal end 120. The distal end 120 is so designated since it is the end that exits the delivery catheter 200 first and thus is more distal to the physician. Distal end 120 is the most tapered and hence the smallest diametered end. Preferably, the taper is such that the distal end 120 is almost closed. By closed it is meant that spirals 140 come closer in closer together at the distal end such that the spiral is tight that there is virtually no lumen 160 inside. The taper begins at the proximal end 180 and is thus associated with the largest diameter lumen.

Figure 11:
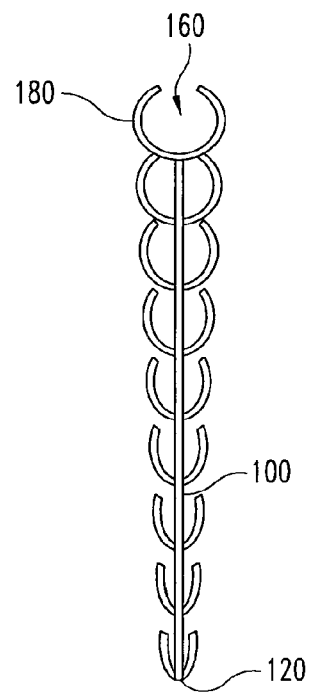
Figure 12:
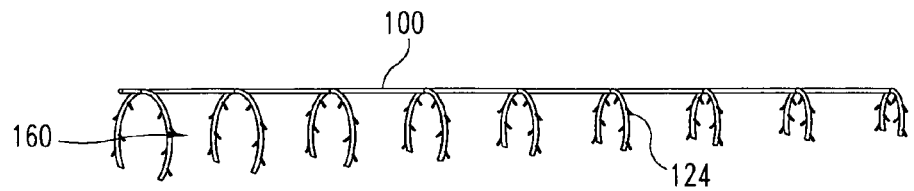

With reference to FIG. 11, it shows the above or top view of the present invention. FIG. 12 shows the thrombogenic fibrils 124 attached to the spirals 140 in the central backbone 100. Although fibrils 124 are shown in FIG. 12, the fibrils 124 can exist in any embodiment.

With reference to FIG. 13, it shows the delivery catheter 200 pushing out the invention. The site of the intended occlusion 240 is shown. If the device is made of the shape memory or expandable material, or the material is in a compressed state, then upon release from the delivery catheter 200, the device expands. Since the largest diameter 260 exits last, the distal end 120 in the rest of the main body of the device, is generally situated at the occlusion site 240. Neither the catheter is pressed away nor is there any pushing of the vessel 220 away is achieved. The pressure exerted by the device against the walls of the vessel 220 is by the radially expanding spirals.

Figure 14:
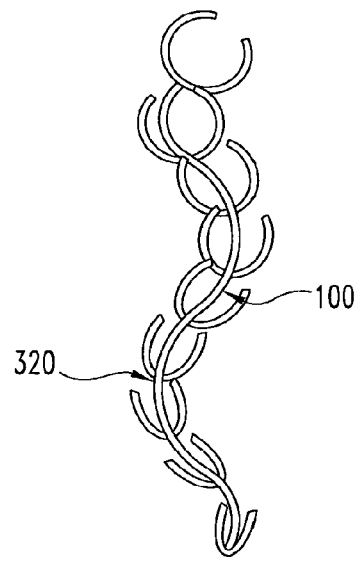

With respect to FIG. 14, in another embodiment of the invention, the backbone 100 may be zig zagged 320 so that it permits easier loading into the catheter 200. Plus it imparts a springlike feature to the backbone such that if the occlusion device is intended for a vessel 220 that moves, pivots, or twists, such as a carotid neck artery, then it will bend as desired without undue stress on the backbone.

Figure 15:
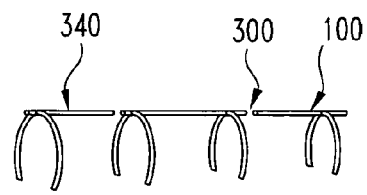

FIG. 15 shows another embodiment of the present invention. The device may be cut at particular joints 300 such that the physician can custom size the device to vary the speed or rate of occlusion. Segments 340 can be cut off at the proximal or distal end. Cutting off the various segments permits varying diameters to be inserted.

The material can be made of any thrombogenic material to promote thrombus formation. In addition, the material could be collagenous biomaterials as described above. The collagenous biomaterial can be hardened by crosslinking. Since the collagenous biomaterial is a biodegradable material, the occlusion will occur but the patient will not have any metallic substances remaining in the body. Thus a total collagenous biomaterial is a preferred material since it will leave behind an all natural blockage. Thus depending on the intent of the doctor, a synthetic material or natural material could be used.

The invention promotes a clinical advantage in that the wire is not made of a continuous coil, can be made with an all natural material, presents a method of varying the sizes of the lumens by cutting off various segments to fit.

The device may also be partially or completely coated with various thrombus causing medicaments or agents, or other pharmacologic agents, such as those that reduce inflammation, cancers, at the spots where the device meets with the lumen wall. Thus, the device can be taxol coated also.

In yet another embodiment of the invention, the device may comprise a partial collagenous biomaterial and non-collagenous biomaterial. For example the central backbone may be metallic with the spirals being collagenous. Even the backbone or the spirals can be coated, either partially or entirely, with pharmacologic agent, such as taxol. In addition, the device may be half collagenous and half metallic.

Figure 16:
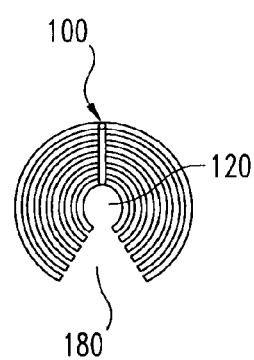

FIG. 16 shows an aerial view looking down through the proximal (large diameter end) to the distal end (small diameter end).

If the material is made from collagenous biomaterials, such as small intestine submucosa (SIS), the SIS can be strengthened to make it more rigid. Some treatment includes methacrylate, polyglycolic acid, or other stiffeners. It can be more rigid by adding more material.

The frame could be made by forming a sheet into a tapered tube, freeze drying it, then cutting out the desired pattern, thus leaving an integral (one composition) material. In another embodiment, the spirals could be cut out first, adjusted for size, then attached to another biomaterial backbone. Thus, the biomaterial could be made to expand upon exiting the catheter.

It will be appreciated that variations of the above-described processing procedures are intended to be within the scope of this invention. For example, the source tissue for the collagenous biomaterial, e.g., stomach, whole intestine, cow uterus and the like, can be partially delaminated, treated with a disinfecting or sterilizing agent followed by complete delamination of the tela submucosa. Illustratively, attached mesentery layers, and/or serosa layers of whole intestine can be advantageously removed prior to treatment with the disinfecting agent, followed by delamination of remaining attached tissues from the tela submucosa 12. These steps can or can not be followed by additional disinfection steps, e.g., enzymatic purification and/or nucleic acid removal. Alternatively, the tela submucosa source can be minimally treated with a disinfecting or other such agent, the tela submucosa delaminated from the tunica muscularis and tunica mucosa, followed by a complete disinfection treatment to attain the desired contaminant level(s). All such variations and modifications are contemplated to be a part of the process described herein and to be within the scope of the invention.

Many alterations and modifications can be made by those of ordinary skill in the art without departing from the spirit and scope of the invention. The illustrated embodiments have been shown only for purposes of clarity and examples, and should not be taken as limiting the invention as defined by the appended claims, which include all equivalents, whether now, or later devised.

What is claimed is:

1. A method for achieving full occlusion at a site in the body of a patient, comprising:
   providing an implantable occlusion device for delivery to the site, the occlusion device comprising a remodelable collagenous biomaterial harvested from an animal tissue source and retaining at least one biotropic agent from the animal tissue source, the biotropic agent selected from a proteoglycan, a growth factor, a glycoprotein and a glycosaminoglycan; and
   delivering the occlusion device to the site with the occlusion device remaining at the site for a period of time sufficient for the remodelable collagenous biomaterial to promote cellular invasion and ingrowth into the occlusion device and to become remodeled with tissue of the patient so that an all-natural, remodeled tissue blockage is generated at the site and remains at the site fully occluding the site.

2. The method of claim 1, wherein the remodelable collagenous biomaterial retains a proteoglycan, a growth factor, a glycoprotein and a glycosaminoglycan from the animal tissue source.

3. The method of claim 1, wherein the remodelable collagenous biomaterial retains one or more growth factors from the animal tissue source.

4. The method of claim 1, wherein the remodelable collagenous biomaterial is selected from the group consisting of pericardium, basement membrane, amniotic membrane, mucosa and submucosa.

5. The method of claim 1, wherein the remodelable collagenous biomaterial has not been treated with a chemical crosslinking agent.

6. A method for achieving full occlusion at a site in the body of a patient, comprising:
   providing an implantable occlusion device for delivery to the site, the device comprising a harvested remodelable collagenous material effective to promote new tissue growth at the site, wherein the remodelable collagenous biomaterial retains at least one bioactive agent selected from the group consisting of a proteoglycan, a growth factor, a glycoprotein and a glycosaminoglycan; and
   delivering the occlusion device to the site so as to cause a full occlusion and full blockage of the site.

7. The method of claim 6, wherein the remodelable collagenous biomaterial exhibits an angiogenic character.

8. The method of claim 6, wherein the remodelable collagenous biomaterial has not been treated with a chemical crosslinking agent.

9. The method of claim 6, wherein the remodelable collagenous biomaterial includes a proteoglycan, a growth factor, a glycoprotein and a glycosaminoglycan.

10. The method of claim 6, wherein the remodelable collagenous biomaterial retains one or more growth factors in the collagenous material.

11. The method of claim 6, wherein the remodelable collagenous biomaterial comprises submucosa.

12. The method of claim 11, wherein the submucosa comprises porcine submucosa.

13. The method of claim 11, wherein the submucosa comprises small intestine submucosa, urinary bladder submucosa or stomach submucosa.

14. The method of claim 6, wherein the remodelable collagenous biomaterial includes lyophilized collagenous material.

15. The method of claim 6, wherein the remodelable collagenous biomaterial includes non-lyophilized collagenous material.

16. The method of claim 6, wherein the remodelable collagenous biomaterial is selected from the group consisting of pericardium, basement membrane, amniotic membrane, mucosa and submucosa.

17. The method of claim 6, wherein the occlusion device includes a pharmacologic agent disposed on the remodelable collagenous material.

18. The method of claim 6, wherein the remodelable collagenous biomaterial has not been treated with a chemical crosslinking agent.

* * * * *